United States Patent
Sezi et al.

[11] Patent Number: 6,156,902
[45] Date of Patent: Dec. 5, 2000

[54] BIS-O-AMINO (THIO) PHENOLS, AND THEIR PREPARATION

[75] Inventors: Recai Sezi, Röttenbach; Michael Keitmann, Weisendorf; Andreas Weber, Ursensollen, all of Germany

[73] Assignee: Infineon Technologies AG, Munich, Germany

[21] Appl. No.: 09/161,549

[22] Filed: Sep. 24, 1998

[30] Foreign Application Priority Data

Sep. 24, 1997 [DE] Germany .................. 197 42 196

[51] Int. Cl.[7] .................. C07D 211/72; C07C 221/00
[52] U.S. Cl. .................. 546/296; 564/328; 564/329; 564/335
[58] Field of Search .................. 564/328, 329, 564/335; 546/296

[56] References Cited

U.S. PATENT DOCUMENTS

| | | |
|---|---|---|
| 4,395,482 | 7/1983 | Ahne et al. . |
| 4,525,539 | 6/1985 | Feiring . |
| 5,106,720 | 4/1992 | Mueller et al. . |
| 5,831,127 | 11/1998 | Saito et al. . |

FOREIGN PATENT DOCUMENTS

| | | |
|---|---|---|
| 0023662 | 5/1983 | European Pat. Off. . |
| 0317942 | 5/1989 | European Pat. Off. . |
| 0264678 | 9/1991 | European Pat. Off. . |
| 0300326 | 6/1993 | European Pat. Off. . |
| 1205518 | 9/1986 | U.S.S.R. . |

OTHER PUBLICATIONS

Chemical Abstracts XP–002088350, vol. 106 (1987), p. 10.
Chemical Abstracts XP–002088351, vol. 120 (1994), p. 2.
Chemical Abstracts XP–002088424, vol. 92 (1980), p. 24.

*Primary Examiner*—Paul J. Killos
*Attorney, Agent, or Firm*—Herbert L. Lerner; Laurence A. Greenberg; Werner H. Stemer

[57] ABSTRACT

The invention relates to novel bis-o-aminophenols, and bis-o-aminothiophenols of the following structure:

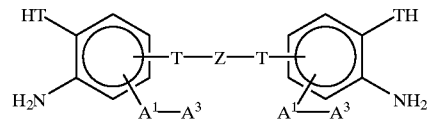

where $A^1$ to $A^3$ are—independently of one another—H, $CH_3$, $OCH_3$, $CH_2CH_3$, or $OCH_2CH_3$ T is O or S, and Z is a carbocyclic or heterocyclic aromatic radical.

18 Claims, No Drawings

BIS-O-AMINO (THIO) PHENOLS, AND THEIR PREPARATION

BACKGROUND OF THE INVENTION

FIELD OF THE INVENTION

The invention relates to novel bis-o-aminophenols and bis-o-aminothiophenols, which are also jointly abbreviated to bis-o-amino(thio)phenols, and to a process for their preparation.

Bis-o-aminophenols are needed, in particular, for the preparation of high-temperature-stable polymers, such as polybenzoxazoles (PBOs) and their precursors and for the preparation of hydroxypolyimides (in this respect, see, for example, EP 0 264 678 B1 and EP 0 300 326 B1). PBO precursors can be prepared by reacting a dicarboxylic acid chloride with a bis-o-aminophenol. However, whereas numerous dicarboxylic acids and chlorides thereof are available owing to the wide variety of potential industrial applications, there are comparatively few bis-o-aminophenols. In addition the nature of the aminophenol used has a strong effect on the property profile of the polymer prepared therewith. For example, not only the thermal, electrical and mechanical behavior, but also the solubility and hydrolysis stability and numerous other properties of the polymer are greatly affected by the aminophenol used in the preparation. PBO precursors in the form of a photosensitive composition can be structured inexpensively by direct methods, i.e. without an auxiliary resist. Compared with other dielectrics which can be photostructured directly, such as polyimide (PI) and benzocyclobutene (BCB), PBO precursors offer the advantage of positive structurability and aqueous-alkaline development (see EP 0 023 662 B1 and EP 0 264 678 B1). To this end, the PBO precursors used must be substantially transparent at the exposure wavelength and sufficiently soluble in the developer, which preferably contains no metal ions. Like polyimides, polybenzoxazoles also have the major advantage that, compared with the cyclized final product, they can be applied to a substrate as readily soluble precursors and then cyclized, during which the solubility and thus the sensitivity to solvents and other process chemicals decreases greatly.

In addition to good electrical, mechanical and thermal properties, use of polybenzoxazoles in microelectronics, in particular as dielectric between two metal planes, for example in multi-chip modules and memory and logic chips, or as buffer coat between the chip and its housing, also requires low moisture absorption; this is because the moisture content in the polymer layer impairs the electrical properties of the polymer and also can result in bubble formation and flaking at high temperatures. A good planarization capacity of the polybenzoxazoles is likewise advantageous since production of components using a dielectric which produces good planarization allows expensive polishing procedures (chemical mechanical polishing, CMP) to be avoided.

Aminophenols which are suitable for the preparation of readily soluble PBO precursors are disclosed, for example, in U.S. Pat. No. 4,525,539 and EP 0 317 942 A2. However, there is no indication therein of the moisture absorption or planarization behavior of the resultant polymers after cyclization on the substrate (see EP 0 264 678 B1 and EP 0 317 942 A2). In the preparation of the aminophenols, a phenolic starting compound is nitrated. If the nitration does not take place completely, i.e. to 100%, and entirely free from isomers, i.e. nitration may only take place in the o-position to the hydroxyl group, reduction of the nitro group in some cases results in aminophenols, which do not allow complete cyclization in the PBO precursor and considerably impair the properties of the polybenzoxazole. This is a major disadvantage of the known preparation processes.

SU 1 205 518 A discloses aromatic aminophenols. However, polybenzoxazoles prepared from these aminophenols are not stable at high temperatures, showing 1% weight loss already at 420–430° C. The preparation of these aminophenols also uses carcinogenic hydrazine hydrate, which is a considerable disadvantage. In addition, there is again no indication of the moisture absorption and planarization behavior of the resultant polymers after cyclization on the substrate.

A process for the preparation of bisaminophenols is also disclosed in "Polymer Preprints" 34 (1), 1993, pages 425 and 426. This process has the disadvantage of requiring high temperatures, i.e. significantly higher temperatures than 100° C. (solutions in dimethylacetamide and toluene are refluxed). However, high reaction temperatures promote side reactions, which reduce the yield (which is a maximum of 73%) and make purification of the target product more difficult. There is likewise no indication herein of the moisture absorption or planarization behavior of the resultant polymers after cyclization on the substrate.

SUMMARY OF THE INVENTION

The object of the invention is to provide novel bis-o-aminophenols and bis-o-aminothiophenols which are particularly suitable for the preparation of polymers which satisfy the greatly increased demands of microelectronics. The bis-o-amino(thio)phenols should, in particular, enable the preparation of readily soluble polymer precursors which, after cyclization on a substrate, give polybenzoxazoles or polybenzothiazoles of low moisture absorption, high heat stability and high degree of planarization. In addition, the bis-o-amino(thio)phenols should be stable on storage and should not change on storage in air.

This object is achieved in accordance with the invention by bis-o-aminophenols and bis-o-aminothiophenols of the following structure:

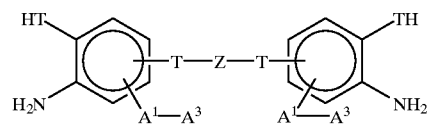

in which $A^1$ to $A^3$ are—independently of one another—H, $CH_3$, $OCH_3$, $CH_2CH_3$, or $OCH_2CH_3$, T is O or S, and Z is one of the following carbocyclic or heterocyclic aromatic radicals:

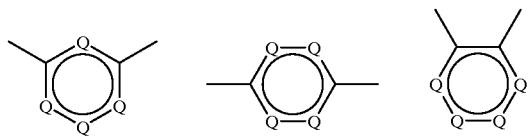

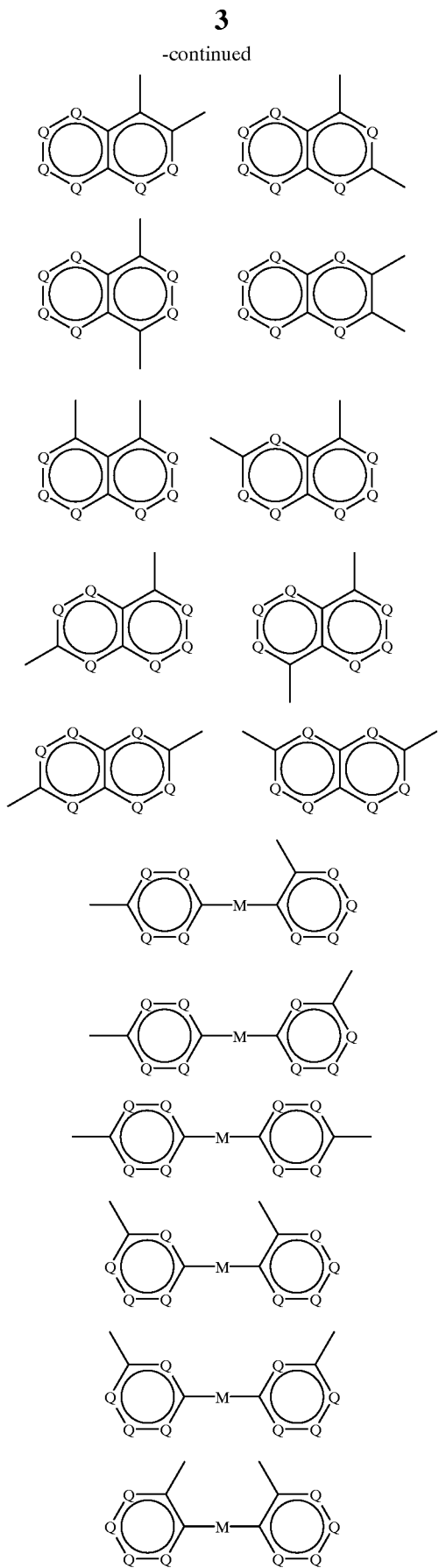

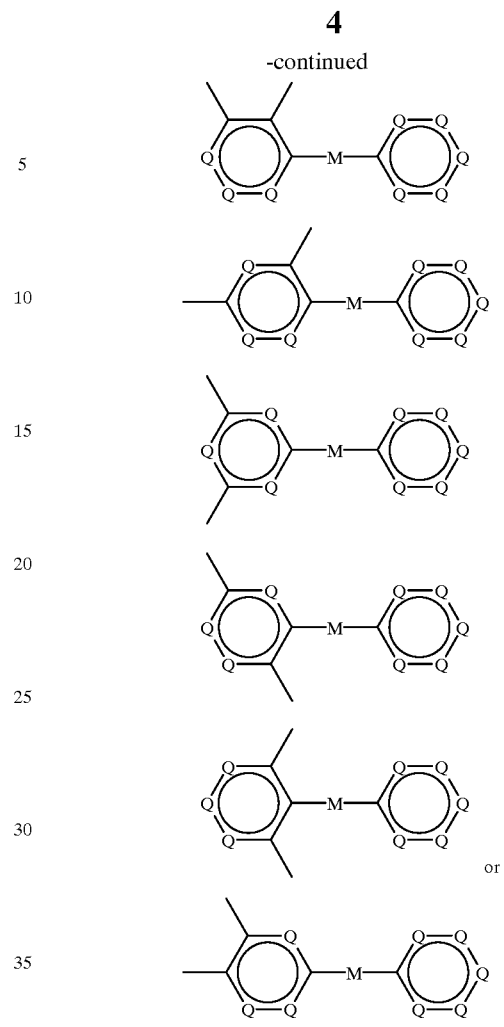

where Q=C—A or N, and A=H, F, $(CH_2)_pCH_3$, $(CF_2)_pCF_3$, $O(CH_2)_pCH_3$, $O(CF_2)_pCF_3$, $CO(CH_2)_pCH_3$, $CO(CF_2)_pCF_3$ where p=0 to 8 (linear or branched chain), $OC(CH_3)_3$, $OC(CF_3)_3$, $C_6H_5$, $C_6F_5$, $OC_6H_5$, $OC_6F_5$, cyclopentyl, perfluorocyclopentyl, cyclohexyl or perfluorocyclohexyl, where, in the isolated aromatic rings, a maximum of 3 N-atoms may be present per ring and only 2 N-atoms may be adjacent, and, in the fused ring systems, a maximum of 2 N-atoms may be present per ring, M=a single bond, $(CH_2)_n$, $(CF_2)_n$, $CH(CH_3)$, $CH(CF_3)$, $CF(CH_3)$, $CF(CF_3)$, $CH(C_6H_5)$, $CH(C_6F_5)$, $CF(C_6H_5)$, $CF(C_6F_5)$, $C(CH_3)(C_6H_5)$, $C(CH_3)(C_6F_5)$, $C(CF_3)(C_6H_5)$, $C(CF_3)(C_6F_5)$, $C(C_6H_5)_2$, $C(C_6F_5)_2$, CO, $SO_2$,

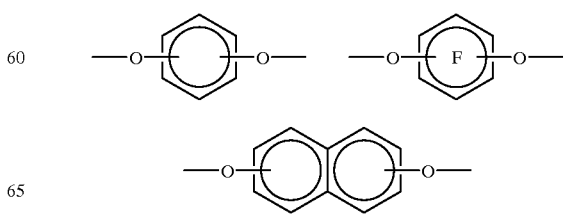

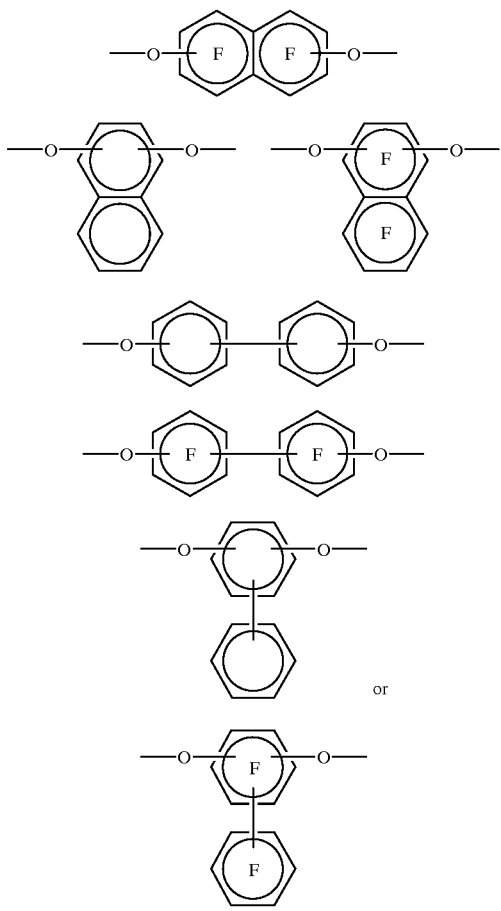

provided that when Z=

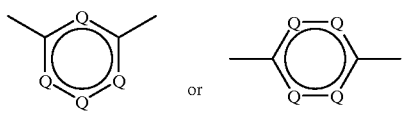

at least one Q group of the bis-o-aminophenol must be N or C—A where A is other than H, and when Z=

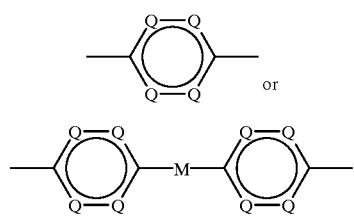

with Q being C—F and M being a single bond, the amino groups of the bis-o-aminophenol must be positioned ortho or para to the oxygen bridge.

The novel compounds have, for example, the following structure:

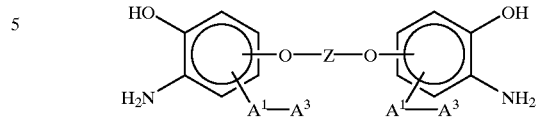

In compounds of this type, the ether bridges are apparently responsible for the good solubility and the good planarization properties of the polymer precursors prepared therewith. By the way, the characterizations "$A^1$–$A^3$" in the structural formula means that the aminophenyl groups contain radicals $A^1$, $A^2$ and $A^3$.

The bis-o-amino(thio)phenols are prepared by (a) reacting a halogen compound of the structure X—Z—X in a solvent at a temperature from 20 to 100° C. with a nitrophenol or nitrothiophenol ("nitro(thio) phenol" for short) of the structure

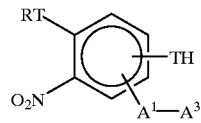

in the presence of at least a stoichiometric quantity of a base or with an alkali metal salt of the nitro(thio) phenol, where X is a halogen atom, $A^1$ to $A^3$, T and Z are as defined above, and R is an alkyl, alkoxyalkyl, alkenyl, alkoxyalkenyl, alkynyl or alkoxyalkynyl group, each having a maximum of 6 carbon atoms; a phenyl, phenacyl or benzyl group; a benzylalkyl, benzylalkenyl, benzyloxyalkyl, benzyloxyalkenyl, benzylalkoxyalkyl or benzylalkoxyalkenyl group, each having a maximum of 4 aliphatic carbon atoms; and (b) reducing the resultant bis-o-nitro(thio)phenol to the bis-o-amino(thio)phenol and removing the group R.

The process of the invention does not give rise to any of the problems which occur in the prior art. Polybenzoxazoles derived, for example, from bis-o-aminophenols prepared according to this invention and having the structure

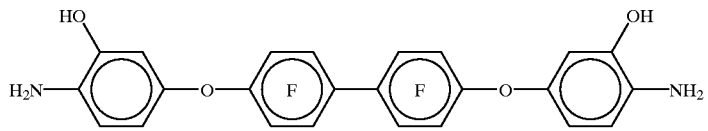

are clearly more stable at high temperature (1% weight loss only at 480° C.) than structurally similar polybenzoxazoles according to SU 1 205 518 A having the hydroxyl group para to the ether bridge and the amino group in the meta position (1% weight loss at 420–430° C.)

DESCRIPTION OF PREFERRED EMBODIMENTS

The dihalide compounds X—Z—X are aromatic or substituted aromatic compounds (where X=halogen). Suitable compounds for the reaction with the nitro(thio)phenol can be perhalogenated or partially halogenated compounds with at least two halogen atoms, with partially or fully fluorinated compounds particularly preferred. Examples of such compounds are 1,2,4-trifluorobenzene, 2,3,5,6-tetrafluorotoluene, octafluorotoluene, 2,3,5,6-tetrafluoro-p-xylene, 2,6-difluoropyridine, 2,3,5.6-tetrafluoropyridine, pentafluoropyridine, decafluorobiphenyl and decafluorobenzophenone.

It is essential for the R protected hydroxyl or mercapto group of the nitro(thio)phenol to be ortho to the nitro group. The preparation of nitro(thio)phenols with a protected hydroxyl or mercapto group ortho to the nitro group is described in the simultaneously filed German patent application serial no. 197 42 135.0 "o-Nitro(thio)phenol derivatives and their preparation" (GR 97 P 3683).

The protecting group R is preferably an alkyl, alkoxyalkyl, phenyl, or benzyl group, and it is important for the group RT to be stable during the reaction of the halogen compound with the nitro(thio)phenol but subsequently removable.

The reaction between the halogen compound and the nitro(thio)phenol, in which ether or thioether bridges are formed, is carried out in the presence of a base. This base is preferably a carbonate or hydrogencarbonate of an alkali metal or alkaline earth metal, such as sodium carbonate or potassium carbonate, or an organic base containing a tertiary N atom, for example triethylamine or pyridine. The nitro (thio)phenol can also be replaced by a corresponding alkali metal salt, for example the potassium salt, in which case added base is not necessary for the reaction with the dihalide.

A reaction temperature in the range from 20 to 80° C. has proven suitable. Temperatures not above 80° C. are preferred owing to the greater selectivity of the reaction. This is because the yields here are more than 90%, which represents a significant advantage compared to the prior art.

Suitable solvents are, in particular, dimethylformamide, diethylformamide, dimethylacetamide, dimethyl sulfoxide, N-methylpyrrolidone, γ-butyrolactone, acetonitrile, tetrahydrofuran and pyridine. In principle, however, all polar aprotic solvents in which the starting compounds are soluble can be used.

The reduction of the dinitro compound can be carried out, for example, by hydrogenation using hydrogen on Pd/C. In principle, however, all processes which are suitable for reducing a nitro group to an amino group are suitable.

Reduction of the dinitro compound and removal of the protective group R can be accomplished in two separate process steps, whereby the protective group is removed for example by reaction with trifluoroacetic acid or titanium tetrachloride. Preferably, however, reduction of the nitro group and removal of the protective group are accomplished simultaneously by hydrogenation with hydrogen and palladium/carbon catalyst.

The hydrogenation is preferably carried out at temperatures of from 25 to 50° C. Suitable solvents are esters and ethers, for example ethyl acetate and tetrahydrofuran.

The polymer precursors prepared from the bis-o-amino (thio)phenols of the invention are readily soluble in many organic solvents, such as acetone, ethyl lactate, N-methylpyrrolidone, diethylene glycol mono- or diethyl ether, cyclohexanone and γ-butyrolactone, and in aqueous-alkaline developers containing no metal ions. They are therefore highly suitable as base polymers for dielectrics which can be photostructured positively and can be developed in aqueous-alkaline media. The precursors can easily be applied to substrates, such as silicon wafers, by spin-coating methods, they form uniform films, and can readily be cyclized on the substrate. A particular advantage of the precursors prepared from these bis-o-amino(thio)phenols is their high planarization capacity and low moisture absorption.

The invention will be illustrated in greater detail below with reference to working examples.

EXAMPLE 1

Preparation of 4,4'-Bis(4-nitro-3-benzyloxyphenoxy)octafluorobiphenyl

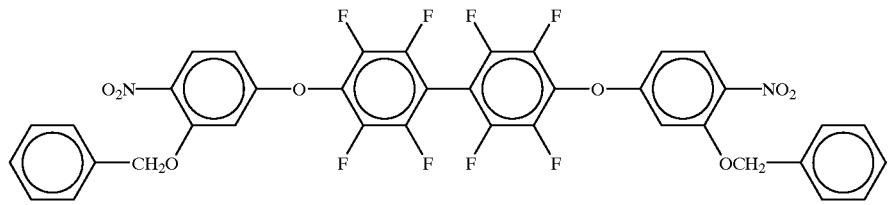

24.5 g of 5-hydroxy-2-nitrophenylbenzylether (0.1 mol) and 16.7 g of decafluorobiphenyl (0.05 mol) are dissolved in 270 ml of dry dimethyl sulfoxide in a three-neck flask fitted with reflux condenser, nitrogen inlet and stirrer. 30 g of potassium carbonate (0.22 mol) are added to the solution and the mixture is heated in a temperature-controllable oil bath at 100° C. for 4 hours. The reaction solution is then allowed to cool to room temperature, and the residue is filtered off via a fluted filter. The solution is then added to 500 ml of water and concentrated hydrochloric acid is added until the solution is acidic. During this addition, a yellow reaction product precipitates, and is filtered off via a Büchner funnel and washed three times with water. The reaction product is then recrystallized from a mixture of methanol and methylene chloride (volume ratio 1:1) and then dried for 48 hours under nitrogen at 40° C./10 mbar in a vacuum drying cabinet (yield: 94%).

Characterization:

Mass spectrum: molecular peak at 784;
Elemental analysis:

| Mass spectrum: | molecular peak at 784 | | |
| --- | --- | --- | --- |
| Elemental analysis: | | | |
| Theoretical value (in %): | C: 58.2 | H: 2.6 | N: 3.6 |
| Found (in %): | C: 58.2 | H: 2.5 | N: 3.7 |
| m.p.: | 212° C. | | | m.p.: 212° C.

EXAMPLE 2

Preparation of 4,4'-Bis(4-amino-3-hydroxyphenoxy) octafluorobiphenyl

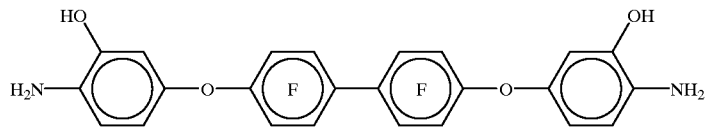

72 g of 4,4'-Bis(4-nitro-3-benzyloxyphenoxy) octafluorobiphenyl prepared as described in Example 1 (0.09 mol) are dissolved in 600 ml of a mixture of tetrahydrofuran and ethyl acetate (volume ratio 1:1), and 7 g of Pd/C (palladium/carbon) are added to the solution. The mixture is then hydrogenated at room temperature in an autoclave with vigorous stirring using hydrogen at a pressure of 1 bar; after 7 days, the reaction is terminated. The yellow-beige solution is evaporated to half in a rotary evaporator and left to stand overnight at room temperature, during which the reaction product precipitates in crystalline form. The reaction product is then collected and dried for 48 hours under nitrogen at 40° C./10 mbar in a vacuum drying cabinet (yield: 96%0).

Characterization:

Mass spectrum: molecular peak at 544;

Elemental analysis:

| Theoretical value (in %): | C: 53.0 | H: 2.2 | N: 5.1 |
| --- | --- | --- | --- |
| Found (in %): | C: 52.8 | H: 2.3 | N: 5.2 |
| m.p.: | 245° C. | | | m.p.: 245° C.

EXAMPLE 3

Preparation of 4,4'-Bis(4-nitro-3-benzyloxyphenoxy)octafluorobenzophenone

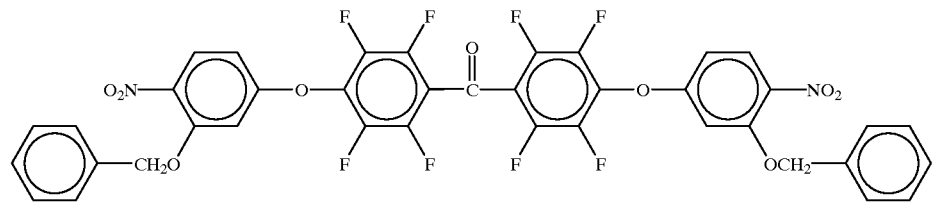

28.3g of 5-hydroxy-2-nitrophenylbenzylether potassium salt (0.1 mol) and 18.1 g of decafluorobenzophenone (0.05 mol) are dissolved in 300 ml of dry acetonitrile in a three-neck flask fitted with reflux condenser, nitrogen inlet and stirrer. The mixture is then stirred at room temperature for 24 hours and filtered through a fluted filter. The clear solution is then evaporated to half in a rotary evaporator and the precipitated yellow-beige reaction product recrystallized from ethyl acetate and dried for 48 hours under nitrogen at 40° C./10 mbar in a vacuum drying cabinet (yield: 92%).
Characterization:
Mass spectrum: molecular peak at 812;
Elemental analysis:

| Mass spectrum: | molecular peak at 812 | | |
|---|---|---|---|
| Elemental analysis: | | | |
| Theoretical value (in %): | C: 57.6 | H: 2.5 | N: 3.4 |
| Found (in %): | C: 57.4 | H: 2.6 | N: 3.4 |
| m.p.: | 167° C. | | | m.p.: 167° C.

EXAMPLE 4

Preparation of 4,4'-Bis(4-amino-3-hydroxyphenoxy) octafluorobenzophenone

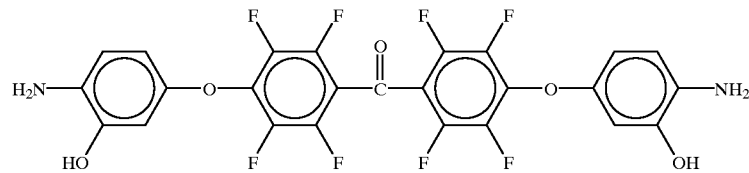

32.5 g of 4,4'-bis(4-nitro-3-benzyloxyphenoxy) octafluorobenzophenone prepared as described in Example 3 (0.04 mol) are dissolved in 500 ml of a mixture of tetrahydrofuran and ethyl acetate (volume ratio 1:1), and 3 g of Pd/C (palladium/carbon) are added to the solution. The mixture is then hydrogenated at room temperature in an autoclave with vigorous stirring using hydrogen at a pressure of 1 bar; after 3 days, the reaction is terminated. The yellow-beige solution is evaporated to half in a rotary evaporator and 100 ml n-hexane is added, during which the reaction product precipitates in crystalline form. The reaction product is then collected and dried for 48 hours under nitrogen at 40° C./10 mbar in a vacuum drying cabinet (yield: 95%).

Characterization:

Mass spectrum: molecular peak at 572;

Elemental analysis:

| Mass spectrum: | molecular peak at 572 | | |
|---|---|---|---|
| Elemental analysis: | | | |
| Theoretical value (in %): | C: 52.5 | H: 2.1 | N: 4.9 |
| Found (in %): | C: 52.6 | H: 2.0 | N: 5.0 |
| m.p.: | 208° C. (decomposition) | | | m.p.: 208° C. (decomposition).

EXAMPLE 5

Preparation of 2,4-bis(4-nitro-3-benzyloxyphenoxy)-3,5,6-trifluoropyridine

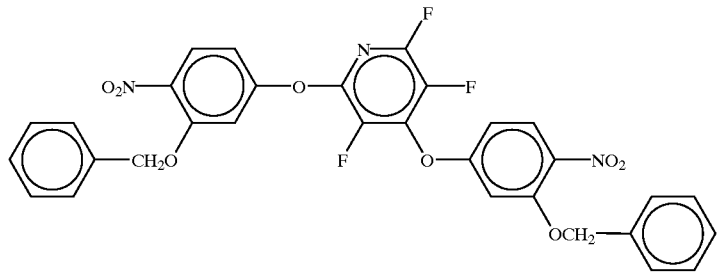

56.6 g of 5-hydroxy-2-nitrophenylbenzylether potassium salt (0.2 mol) are dissolved in 200 ml of dimethylformamide and slowly added drop wise to a solution of 16.9 g pentafluoropyridine (0.1 mol) in 200 ml dimethylformamide. The reaction solution is then stirred 5 days at room temperature, and filtered through a fluted filter. The clear solution is added to 800 ml water and concentrated hydrochloric acid is added until the solution is acidic. From the initially milky solution there precipitates a white reaction product which is collected, washed three times with water and then with a mixture of diethyl ether and methylene chloride (volume ratio 1:1), and dried for 48 hours under nitrogen at 40° C./10 mbar in a vacuum drying cabinet (yield: 93%).

Characterization:

Mass spectrum: molecular peak at 619;

Elemental analysis:

| Mass spectrum:<br>Elemental analysis: | molecular peak at 619 | | |
|---|---|---|---|
| Theoretical value (in %): | C: 60.1 | H: 3.3 | N: 6.8 |
| Found (in %): | C: 59.9 | H: 3.4 | N: 6.9 |
| m.p.: | 135° C. | | | m.p.: 135° C.

EXAMPLE 6

Preparation of 2,4-bis(4-amino-3-hydroxyphenoxy)-3,5,6-trifluoropyridine

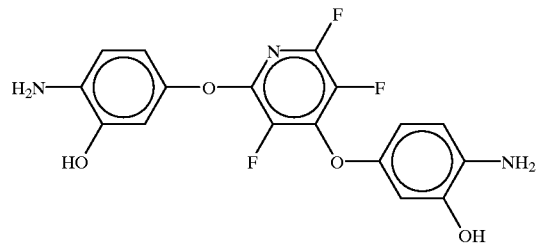

99 g of 2,4-bis(4-nitro-3-benzyloxyphenoxy)-3,5,6-trifluoropyridine prepared as described in Example 5 (0.16 mol) are dissolved in 600 ml of a mixture of tetrahydrofuran and ethyl acetate (volume ratio 1:1), and 10 g of Pd/C (palladium/carbon) are added to the solution. The mixture is then hydrogenated at room temperature in an autoclave with vigorous stirring using hydrogen at a pressure of 1 bar; after 3 days, the reaction is terminated. The yellow-beige solution is evaporated to half in a rotary evaporator and left to stand overnight at room temperature, during which the reaction product precipitates in crystalline form. The reaction product is then collected and dried for 48 hours under nitrogen at 40° C./10 mbar in a vacuum drying cabinet (yield: 93%).

Characterization:

Mass spectrum: molecular peak at 379;

Elemental analysis:

| Mass spectrum:<br>Elemental analysis: | molecular peak at 379 | | |
|---|---|---|---|
| Theoretical value (in %): | C: 53.8 | H: 3.2 | N: 11.1 |
| Found (in %): | C: 53.7 | H: 3.2 | N: 11.1 |

EXAMPLE 7

Preparation of 2,4-bis(4-nitro-3-benzyloxyphenoxy)-1-trifluoromethyl-3,5,6-trifluorobenzene

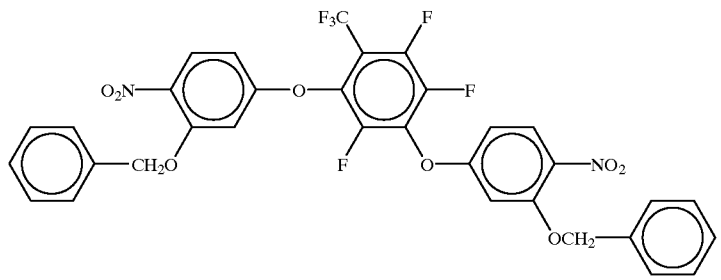

28.3 g of 5-hydroxy-2-nitrophenylbenzylether potassium salt (0.1 mol) are dissolved in 200 ml of dimethylacetamide and added drop wise with stirring at 0° C. to a solution of 23.6 g octafluorotoluene (0.1 mol) in 200 ml dimethylacetamide. The mixture is then stirred 1 hour at room temperature and 3 days at 50° C., and filtered via a fluted filter. The clear solution is added to 600 ml water and concentrated hydrochloric acid is added until the solution is acidic. From the initially milky solution there precipitates a white reaction product which is collected, washed three times with water and then with a mixture of diethyl ether and methylene chloride (volume ratio 1:1), and dried for 48 hours under nitrogen at 40° C./10 mbar in a vacuum drying cabinet (yield: 92%).

Characterization:

Mass spectrum: molecular peak at 686;

Elemental analysis:

| Mass spectrum:<br>Elemental analysis: | molecular peak at 686 | | |
|---|---|---|---|
| Theoretical value (in %): | C: 57.7 | H: 2.9 | N: 4.1 |
| Found (in %): | C: 57.8 | H: 2.8 | N: 4.2 |

EXAMPLE 8

Preparation of 2, 4-bis(4-amino-3-hydroxyphenoxy)-1-trifluoromethyl-3,5,6-trifluorobenzene

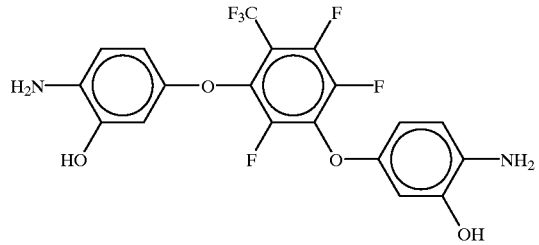

103g of 2,4-bis(4-nitro-3-benzyloxyphenoxy)-1-trifluoromethyl-3,5,6-trifluorobenzene prepared as described in Example 7 (0.15 mol) are dissolved in 600 ml of a mixture of tetrahydrofuran and ethyl acetate (volume ratio 1:1), and 10 g of Pd/C (palladium/carbon) are added to the solution. The mixture is then hydrogenated at room temperature in an autoclave with vigorous stirring using hydrogen at a pressure of 1 bar; after 3 days, the reaction is terminated. The yellow-orange solution is evaporated to half in a rotary evaporator and left to stand overnight at room temperature, during which the reaction product precipitates in crystalline form. The reaction product is then collected and dried for 48 hours under nitrogen at 40° C./10 mbar in a vacuum drying cabinet (yield: 95%)

Characterization:

Mass spectrum: molecular peak at 446;

Elemental analysis:

| Mass spectrum: | molecular peak at 446 | | |
|---|---|---|---|
| Elemental analysis: | | | |
| Theoretical value (in %): | C: 51.1 | H: 2.7 | N: 6.3 |
| Found (in %): | C: 50.8 | H: 2,8 | N: 6.3 |

We claim:

1. A bis-o-aminophenol or bis-o-aminothiophenol of the structure

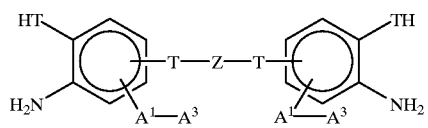

in which $A^1$ to $A^3$ are—independently of one another—H, $CH_3$, $OCH_3$, $CH_2CH_3$, or $OCH_2CH_3$, T is O or S, and Z is one of the following carbocyclic or heterocyclic aromatic radicals;

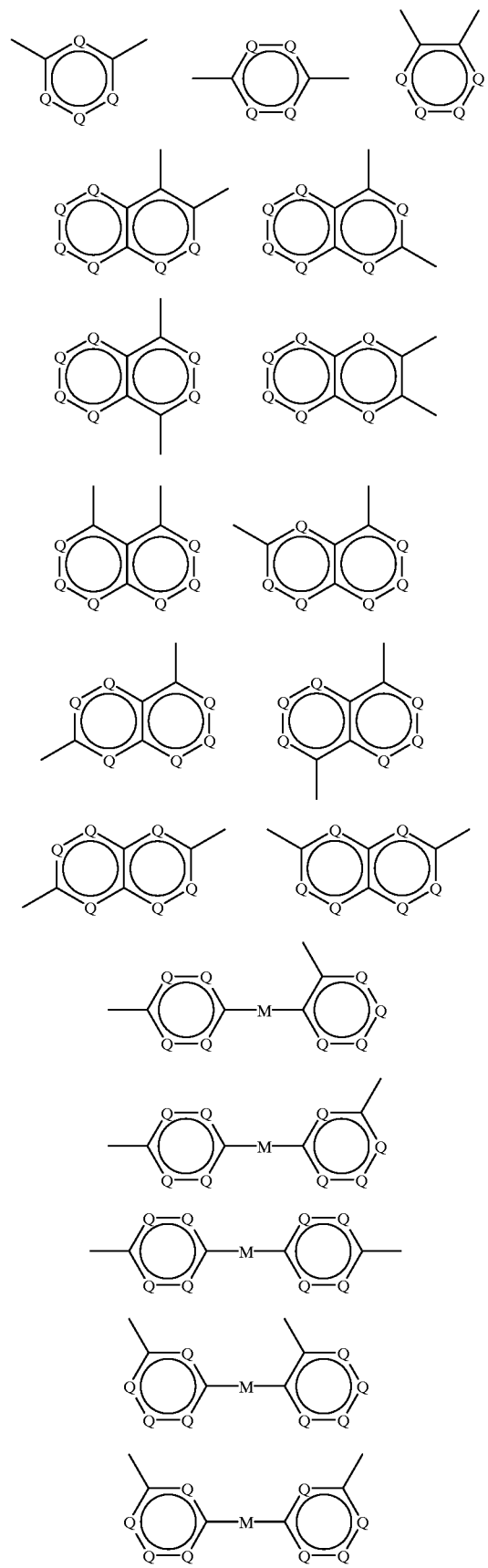

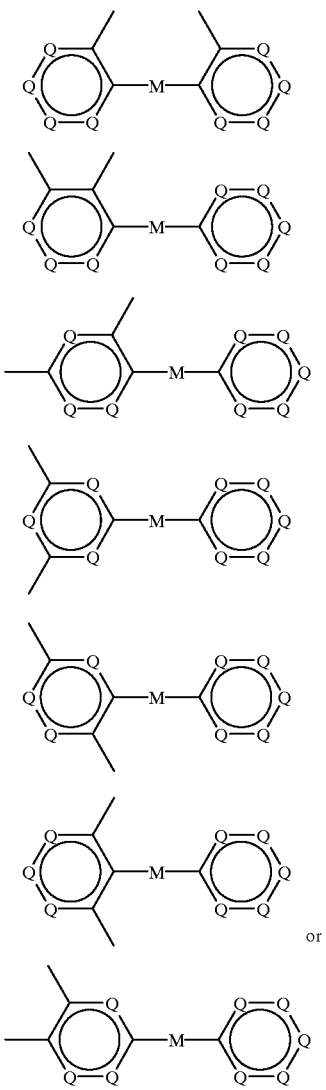

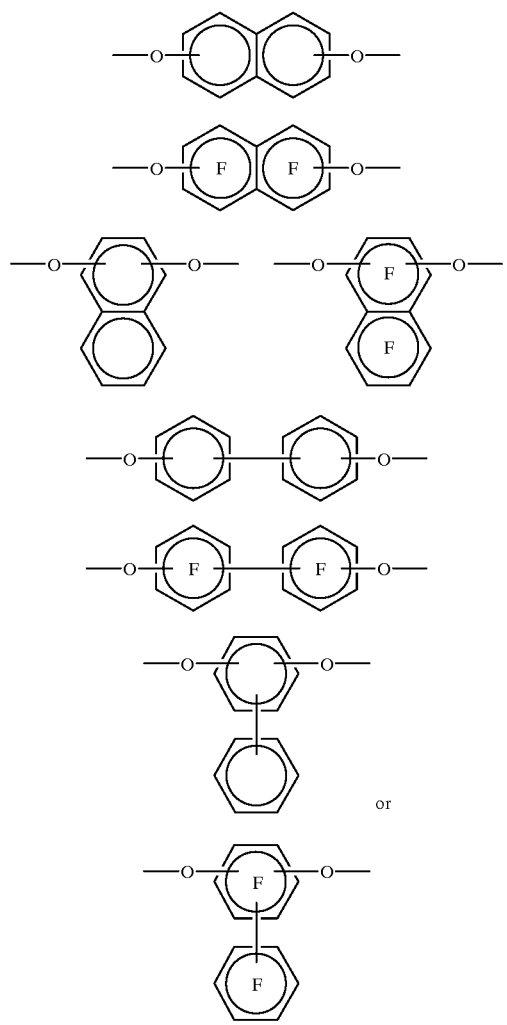

where Q=C—A or N, and A=H, F, $(CH_2)_pCH_3$, $(CF_2)_pCF_3$, $O(CH_2)_pCH_3$, $O(CF_2)_pCF_3$, $CO(CH_2)_pCH_3$, $CO(CF_2)_pCF_3$ where p=0 to 8 (linear or branched chain), $OC(CH_3)_3$, $OC(CF_3)_3$, $C_6H_5$, $C_6F_5$, $OC_6H_5$, $OC_6F_5$, cyclopentyl, perfluorocyclopentyl, cyclohexyl or perfluorocyclohexyl, where, in the isolated aromatic rings, a maximum of 3 N-atoms may be present per ring and only 2 N-atoms may be adjacent, and, in the fused ring systems, a maximum of 2 N-atoms may be present per ring, M=a single bond, $(CH_2)_n$, $(CF_2)_n$, $CH(CH_3)$, $CH(CF_3)$, $CF(CH_3)$, $CF(CF_3)$, $CH(C_6H_5)$, $CH(C_6F_5)$, $CF(C_6H_5)$, $CF(C_6F_5)$, $C(CH_3)(C_6H_5)$, $C(CH_3)(C_6H_5)$, $C(CF_3)(C_6H_5)$, $C(CF_3)(C_6F_5)$, $C(C_6H_5)_2$, $C(C_6F_5)_2$, CO, $SO_2$,

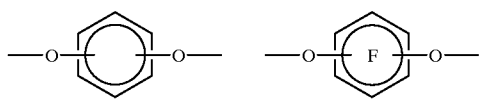

provided that when Z=

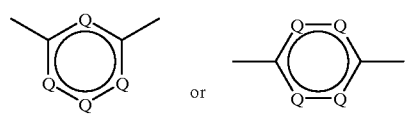

at least one Q group of the bis-o-aminophenol must be N or C—A where A is other than H, and when Z=

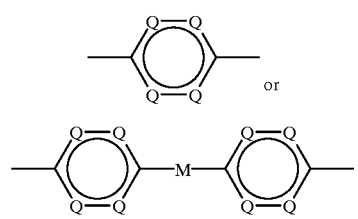

with Q being C—F and M being a single bond, the amino groups of the bis-o-aminophenol must be positioned ortho or para to the oxygen bridge, provided further that, in the bis-o-aminothiophenol, when T in TH is S and Q is C—A with A being H, M when present is not (CF$_2$)$_n$ or CF(CF$_3$).

2. A bis-o-aminophenol according to claim 1 having the structure

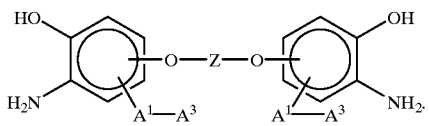

3. A bis-o-aminophenol according to claim 2 in which A$^1$, A$^2$, and A$^3$ are each hydrogen.

4. A bis-o-aminophenol according to claim 2 in which Z is a perfluorinated carbocyclic aromatic radical.

5. A bis-o-aminophenol according to claim 2 in which Z is a perfluorinated heterocyclic aromatic radical.

6. A bis-o-aminophenol according to claim 2 having the structure

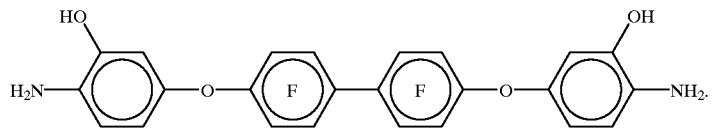

7. A bis-o-aminophenol according to claim 2 having the structure

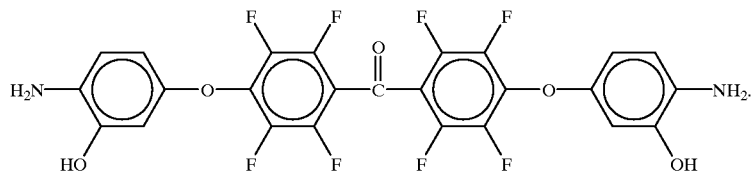

8. A bis-o-aminophenol according to claim 2 having the structure

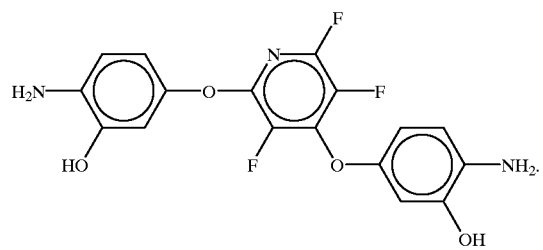

9. A bis-o-aminophenol according to claim 2 having the structure

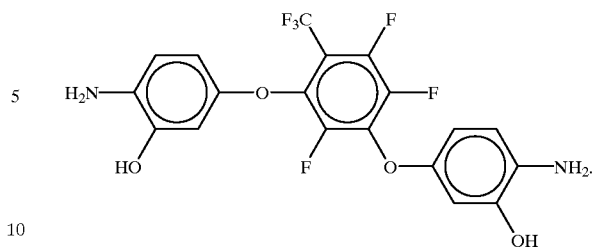

10. A process for the preparation of a bis-o aminophenol or bis-o-aminothiophenol as claimed in claim 1, which comprises (a) reacting a halogen compound of the structure X—Z—X in a solvent at a temperature from 20 to 100° C. with a nitrophenol or nitrothiophenol of the structure

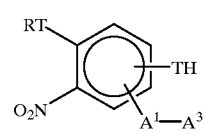

in the presence of at least the stoichiometric quantity of a base or with an alkali metal salt of the nitrophenol or nitrothiophenol,
where X is a halogen atom, A$^1$ to A$^3$, T and Z are as defined above, and R is an alkyl, alkoxyalkyl, alkenyl, alkoxyalkenyl, alkynyl or alkoxyalkynyl group, each having a maximum of 6 carbon atoms; a phenyl, phenacyl or benzyl group; a benzylalkyl, benzylalkenyl, benzyloxyalkyl, benzyloxyalkenyl, benzylalkoxyalkyl or benzylalkoxyalkenyl group, each having a maximum of 4 aliphatic carbon atoms; and (b) reducing the resultant bis-o-nitrophenol or bis-o-nitrothiophenol to the bis-o-aminophenol or bis-o-aminothiophenol and removing the group R.

11. A process as claimed in claim 10, wherein the base is a carbonate or hydrogencarbonate of an alkali metal or alkaline earth metal.

12. A process as claimed in claim 10, wherein the base is an organic base containing a tertiary N-atom.

13. A process as claimed in claim 10, wherein the reduction and removal of the group R is carried out by means of hydrogen and is catalyzed by Pd/C.

14. A process as claimed in claim 10 wherein the nitrophenol is 5-hydroxy-2-nitrophenylbenzylether.

15. A process as claimed in claim 10 wherein the halogen compound X—Z—X is decafluorobiphenyl.

16. A process as claimed in claim 10 wherein the halogen compound X—Z—X is decafluorobenzophenone.

17. A process as claimed in claim 10 wherein the halogen compound X—Z—X is 2.3.5.6-tetrafluoropyridine.

18. A process as claimed in claim 10 wherein the halogen compound X—Z—X is octafluorotoluene.

* * * * *